United States Patent
Hoen (10) Patent No.: US 7,854,015 B2
(45) Date of Patent: Dec. 14, 2010

(54) METHOD FOR MEASURING THE FORCE OF INTERACTION IN A SCANNING PROBE MICROSCOPE

(75) Inventor: Storrs Hoen, Brisbane, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 214 days.

(21) Appl. No.: 12/277,158

(22) Filed: Nov. 24, 2008

(65) Prior Publication Data

US 2010/0132078 A1 May 27, 2010

(51) Int. Cl.
*G01N 13/16* (2006.01)
*G01Q 60/22* (2010.01)
*G01Q 60/24* (2010.01)

(52) U.S. Cl. .............................. 850/33; 850/32; 850/40; 850/1

(58) Field of Classification Search .................... 850/33, 850/32, 40, 1; 382/145
See application file for complete search history.

(56) References Cited

U.S. PATENT DOCUMENTS

2006/0257286 A1* 11/2006 Adams ..................... 422/82.01
2009/0320167 A1* 12/2009 Kobayashi et al. ............ 850/40
2010/0128342 A1* 5/2010 Abramovitch .............. 359/325

* cited by examiner

*Primary Examiner*—Nikita Wells (57) ABSTRACT

A scanning probe microscope and method for operating the same are disclosed. The microscope includes a probe mount for attaching a probe, an electro-mechanical actuator, a probe position signal generator, an impulse signal generator and a servo. A probe tip is mounted on a first end of a cantilever arm, a second end of the cantilever arm being mounted on a mechanical vibrator that causes the second end to vibrate in response to a drive signal. The probe position signal generator generates a position signal indicative of a position of the probe relative to the second end of the cantilever arm. The impulse signal generator measures a quantity related to an impulse imparted to the probe tip by the interaction between the tip and the local characteristics of the sample. The servo operates the electro-mechanical actuator so as to maintain the measured quantity at a predetermined value.

13 Claims, 6 Drawing Sheets

METHOD FOR MEASURING THE FORCE OF INTERACTION IN A SCANNING PROBE MICROSCOPE

BACKGROUND OF THE INVENTION

Scanning probe microscopes enable a class of imaging techniques in which a tip that interacts locally with a sample is scanned over the surface of the sample to generate a three-dimensional image representing the properties of the surface. For example, in contact mode atomic force microscopy, as the tip is moved over the surface of the sample, the arm deflects in response to the changes in topology of the surface. The vertical position of the cantilever arm relative to the sample is adjusted to maintain the arm in a predetermined state. The vertical position as a function of position on the sample can then be used to provide an image of the surface.

Images are typically acquired in one of two modes. In the contact or constant force mode, the tip is brought into contact with the sample and the tip moves up and down as the tip is moved over the surface. The deflection of the arm is a direct measure of force and topographical variations. A feedback controller measures the deflection and adjusts the height of the probe tip so as to maintain constant force between the cantilevered probe and the surface, i.e., the arm is maintained at a fixed deflection. This mode of operation can subject the sample being imaged to excessive shear forces that can alter or damage the sample. This limitation is particularly acute when biological samples or macromolecules are being imaged. Accordingly, some form of non-contact mode of scanning is often preferred for these applications.

In the AC, or non-contact mode, the tip and arm are oscillated at a frequency near the resonant frequency of the arm. The height of the tip can be controlled such that the tip avoids contact with the sample surface, sampling short-range tip/sample forces. Alterations in the short range forces between the tip and the sample result in changes in the oscillation frequency of the tip. Alternatively, the tip can be allowed to make light intermittent contact with the sample only at the bottom of the oscillation cycle. Contact between the probe tip and the sample results in an alteration of the amplitude, phase and/or frequency of the oscillation. The controller adjusts the height of the probe over the sample such that the oscillation amplitude, phase and/or frequency is kept at a predetermined constant value. Since the tip is not in constant contact with the sample, the shear forces applied to the sample are significantly less than in the mode in which the tip is in constant contact. For soft samples, this mode reduces the damage that the tip can inflict on the sample and also provides a more accurate image of the surface in its non-disturbed configuration.

The image is constructed one point at a time and limited by the rate at which the tip can be moved relative to the sample, as well as the time required for the servo loop to reposition the tip vertically, to maintain the distance between the surface and the tip in DC mode, or to keep the oscillation parameter of interest at the predetermined constant value in AC mode. Also, in AC mode, the time needed to detect a change in one or more of the oscillatory parameters of the arm is many periods of the oscillation. Hence, each time the position of the arm is moved relative to the sample, the servo system must wait for a period of time that is long compared to the oscillation period to determine the new amplitude, phase, or frequency of the oscillation and then alter the distance between the arm and the surface to return the oscillatory parameter of interest to the desired value. As a result, the time needed to provide an image can be excessive.

SUMMARY OF THE INVENTION

The present invention includes a scanning probe microscope having a probe mount, an electro-mechanical actuator, a probe position signal generator, and an impulse signal generator. The probe mount receives a probe having a tip that is mounted on a first end of a cantilever arm, a second end of said cantilever arm being mounted on a mechanical vibrator that causes the second end to vibrate at a predetermined frequency in response to a drive signal. The probe tip moves in response to an interaction between the tip and a local characteristic of a sample. The electro-mechanical actuator changes the distance between the sample and the second end of the cantilever arm. The probe position signal generator generates a position signal indicative of a position of the probe relative to the second end of the cantilever arm. The impulse signal generator measures a quantity related to an impulse imparted to the probe tip by the interaction between the tip and the local characteristics of the sample. In one embodiment, the servo operates the electro-mechanical actuator so as to maintain the measured quantity at a predetermined value.

In another aspect of the invention, the impulse signal generator measures a distortion in the position signal that occurs within 2 cycles of the drive signal after the interaction between the tip and sample changes. In yet another aspect of the invention, the impulse signal generator measures a time difference between successive times at which the position signal is equal to a first predetermined threshold value.

DETAILED DESCRIPTION OF THE PREFERRED EMBODIMENTS OF THE INVENTION

Figure 1:
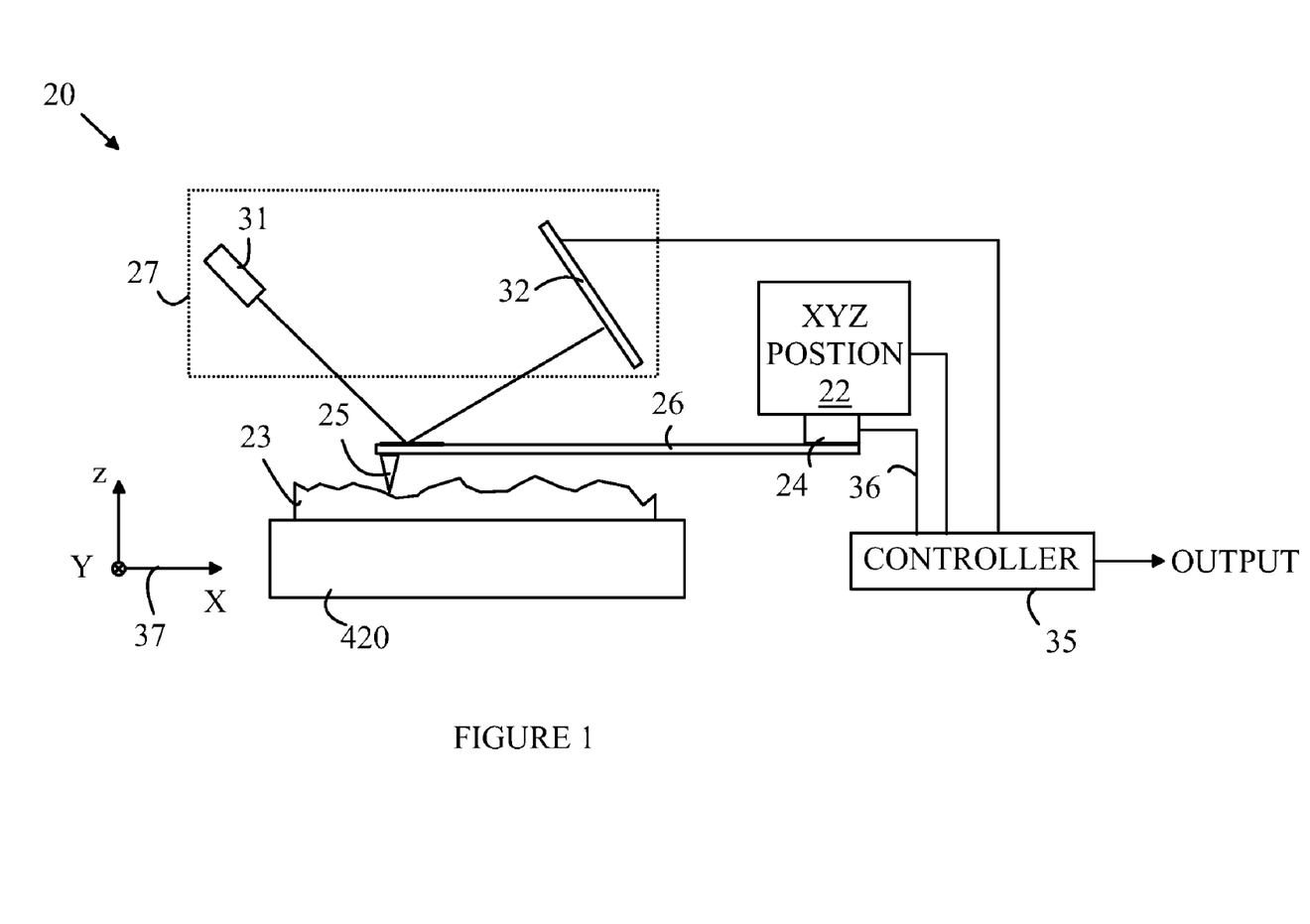
FIG. 1 illustrates one embodiment of an atomic force microscope according to the present invention.

The manner in which the present invention provides its advantages can be more easily understood with reference to FIG. 1, which illustrates one embodiment of an atomic force microscope according to the present invention. Microscope 20 includes a probe assembly and a stage 420 on which a sample 23 to be imaged is mounted. The probe assembly includes a tip 25 that is mounted on a cantilever 26 that deflects in response to forces on probe tip 25. The forces can be the result of a driving force applied to the cantilever that causes the probe to oscillate or to the interaction of the probe tip and the sample. The degree of deflection of cantilever 26 is measured by a detector 27. In the embodiment shown in FIG. 1, the detector 27 includes a light source 31 and a photodetector 32. Light source 31 illuminates a reflective area on cantilever 26, and the location of the reflected light is detected by a photodetector that provides a signal related to the degree of deflection of cantilever 26. However, other methods for measuring the deflection of the cantilever could be utilized. For example, deflection measurements based on interferometric techniques or gratings could be used.

One end of cantilever 26 is attached to an electro-mechanical actuator such as a piezoelectric actuator 22 that can move that end in three dimensions, denoted by x, y, and z as shown at 37. A shaker element 24 that vibrates the fixed end of cantilever 26 is disposed between actuator 22 and cantilever 26 and receives a signal over line 36 that controls the amplitude of the vibrations. Shaker element 24 can be constructed from lead zirconate titanate (PZT) that is driven by an AC drive signal at a frequency $\omega_1$ by controller 35. Here, $\omega_1$ is chosen to be a frequency that is substantially equal to one of the resonant frequencies of cantilever 26. The signal from photodetector 32 includes an AC component at $\omega_1$ that is the result of this induced vibration. This signal will be referred to as the cantilever arm signal in the following discussion.

The cantilever arm signal measures the position of the probe tip relative to the fixed end of the cantilever arm. The amplitude of this signal depends on the interaction between probe tip 25 and sample 23 in the vicinity of probe tip 25, and hence, the amplitude of this signal depends on the distance between tip 25 and the sample and the force of interaction between the tip and the sample as well as the forces exerted by the drive signal. Controller 35 controls the Z-coordinate of the base of the cantilever through actuator 22 to maintain a parameter related to this signal at a predetermined value while the x and y coordinates of the probe tip are varied to provide an image of the sample surface, i.e., the mean height of the cantilever end as a function of x and y, which is output by controller 35.

As noted above, in prior art systems, the amplitude, phase or frequency of the AC component of the arm deflection signal is maintained at a predetermined value during the signal. However, these parameters require a significant time period to measure when the cantilever arm signal changes. The present invention utilizes the measurement of a parameter that is related to the impulse imparted to the probe tip by the interaction with the sample. As will be discussed below, such a parameter can be measured in a time that is small compared to the time needed to detect a change in frequency or the like, and hence, a servo based on such a parameter has a much smaller latency. As a result, the scanning speed of the microscope can be increased.

The present invention is based on the observation that the interaction of the probe tip with the sample results in a distortion of the cantilever arm signal relative to the signal that would be observed if the interaction was not present. To simplify the following discussion, the tip will be said to be close to the specimen if the interaction force between the tip and the specimen is significant over a portion of the tip's vibration cycle. The tip will be said to be far from the sample if the interaction force is negligible over the entire tip vibration cycle. For the purposes of this discussion, a "distortion" of the cantilever arm signal is defined to be a measurable difference between the cantilever arm signal, or a quantity related to the cantilever arm signal, when the tip is interacting with the sample at a first level of interaction compared to the cantilever arm signal, or quantity in question, when the tip is interacting with the specimen at a second level of interaction. For example, the first level of interaction is that obtained when the tip is far from the sample, and the second level of interaction is that obtained when the tip is near the sample.

In comparing the two signals, the signals may be shifted in time relative to one another before the distortion is measured. Denote the signal obtained at the first level of interaction as the reference signal and that obtained at the second level of interaction as the distorted signal. The reference signal may be shifted relative to the distortion signal until the signals are aligned in a predetermined manner prior to measuring the distortion. For example, the reference signal and distorted signals may be shifted such that the signals cross-zero at the same time. The distortion is then measured with respect to the shifted signals.

The minimum distortion that can be detected is related to the optical noise in the cantilever arm signal. The optical noise depends on the particular microscope design. However, for any given optical noise, there is a threshold value that determines the minimum detectable distortion that results from the interaction between the tip and the sample.

The distortion in the cantilever arm signal is measured by comparing the cantilever arm signal, or a parameter related to the cantilever arm signal, when the tip is near the specimen to the cantilever arm signal, or parameter, when the tip is far from the specimen and generating a signal that quantifies the difference in the measurements. The generated signal can then be used to servo the height of the cantilever during the scanning of the specimen.

Figure 2:
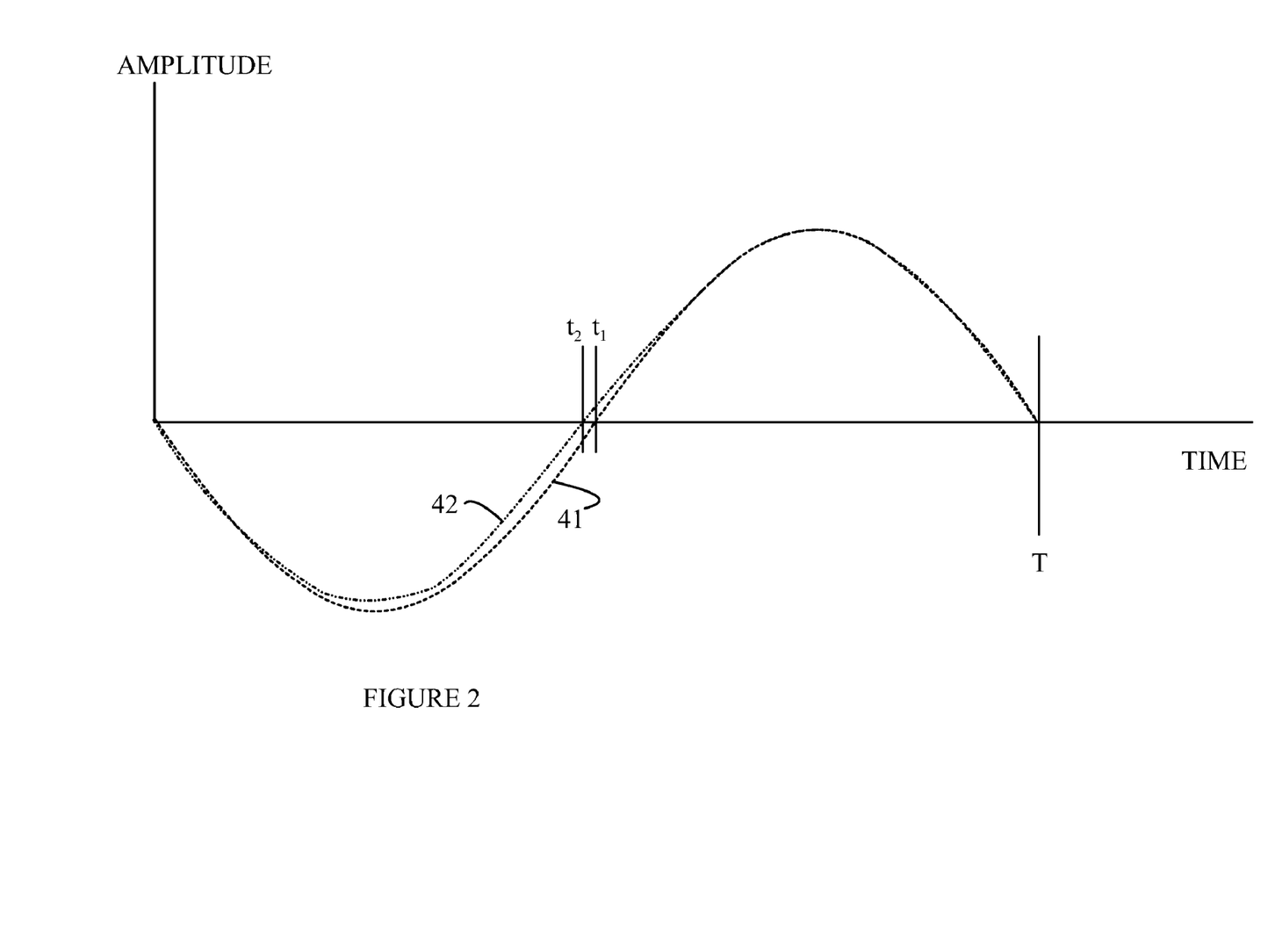
FIG. 2 is a plot of the position signal for the tip on the cantilever arm as a function of time over one cycle of the drive signal.

Refer now to FIG. 2, which is a plot of the position signal for the tip on the cantilever arm as a function of time over one cycle of the drive signal. The drive signal is a sinusoid with a period of T. The position of the tip in the absence of an interaction with the sample is shown at 41. When the tip interacts with the sample, the position curve is distorted as shown at 42.

The distortion of the position signal is related to the force of interaction between the tip and the sample. In particular, the distortion is related to the impulse imparted to the tip by the interaction between the tip and the sample. Hence, by measuring this distortion, a measure of the force of interaction can be obtained. Since the distortion manifests itself in a time that is typically less than one period of the drive signal, changes in the force of interaction can be observed in times that are less than those needed to detect a change in the frequency of the cantilever arm signal.

In one embodiment of the present invention, the distortion in the cantilever arm signal is measured by measuring the difference in the time at which the cantilever arm signal crosses some predetermined voltage or current relative to the time a reference signal crosses that potential. For example, the time at which the cantilever arm signal crosses zero shifts from $t_1$ to $t_2$ when the arm is lowered from a position in which the tip is far from the specimen to a height above the specimen at which the tip interacts with the specimen. In the example shown in FIG. 2, it is assumed that the tip-sample interaction is repulsive, and hence, the amplitude of the cantilever arm signal is reduced by the interaction when the tip is near the bottom portion of the oscillation. When the tip is far from the specimen and the cantilever arm is driven near one of its resonant frequencies, the cantilever arm signal is proportional to the drive signal that is applied to the fixed end of the cantilever arm and shifted in time by some constant phase shift. Hence, by comparing the zero crossing times from the cantilever arm signal with that of the drive signal, a signal that represents the degree of distortion, and hence, a quantity that is monotonically related to the interaction force, can be obtained and used to servo the vertical position of the cantilever arm over the specimen. Embodiments based on other forms of reference signal will be described in more detail below.

Figure 3:
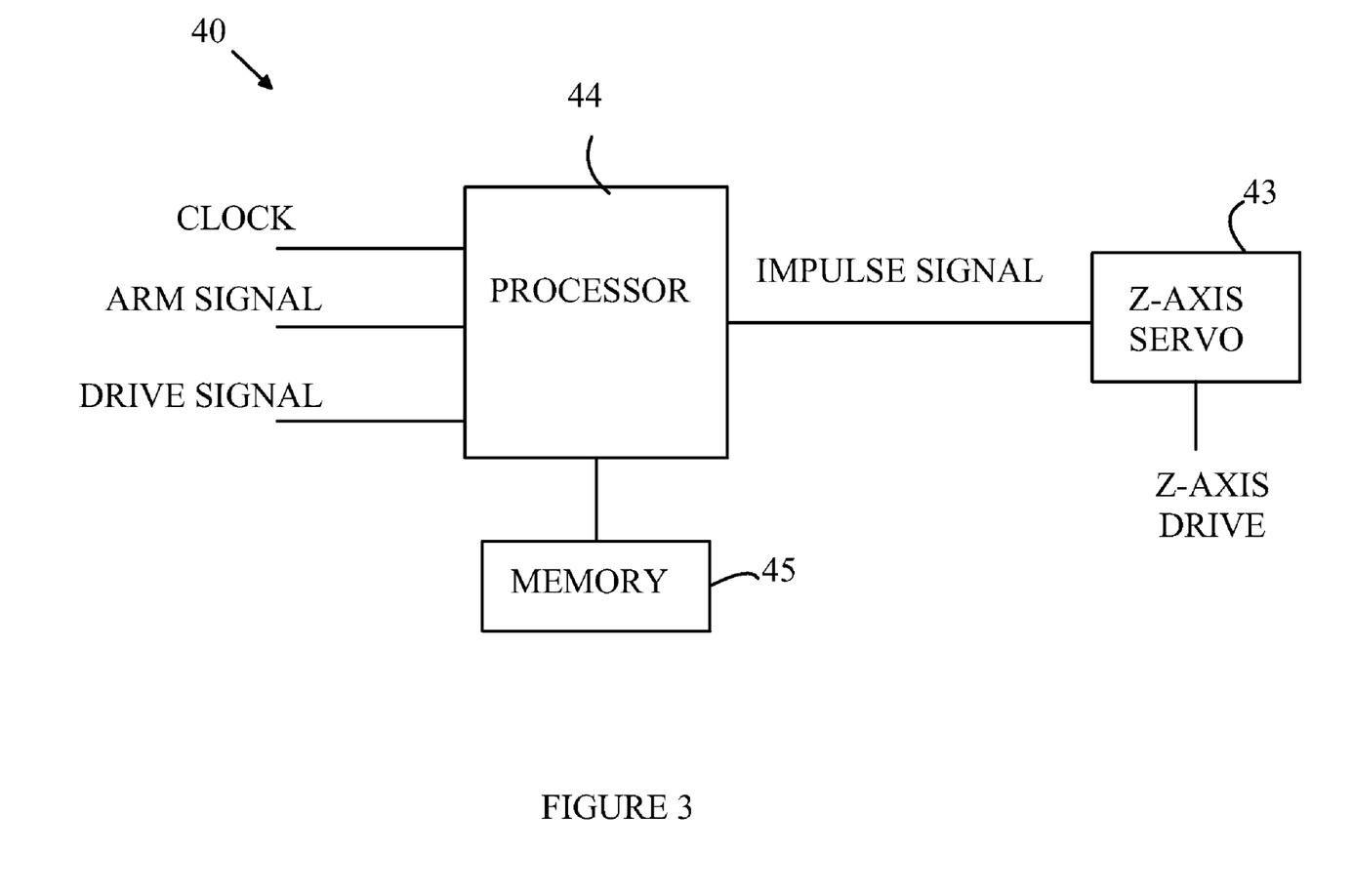
FIG. 3 illustrates an embodiment of an interaction force system that can be included in the embodiment shown in FIG. 1.

Refer now to FIG. 3, which illustrates an embodiment of an interaction force system that can be included in controller 35 shown in FIG. 1. Sub-system 40 includes a processor that receives the cantilever arm signal and optionally, a clock signal and the AC drive signal. In one embodiment, processor 41 uses the clock signal to measure the time interval between the time at which the cantilever arm signal crosses zero while increasing and the time the cantilever arm signal crosses zero while decreasing.

The measured time difference is subtracted from a time difference measured when the tip is sufficiently far from the specimen that no interaction takes place. This reference time difference is stored in a memory 45 connected to processor 44. The difference signal forms a signal that is related to the force of interaction. This "impulse signal" is utilized by z-axis servo 43 to adjust the height of the cantilever over the specimen. That is, the height is adjusted to maintain the impulse signal at a predetermined value.

Figure 4:
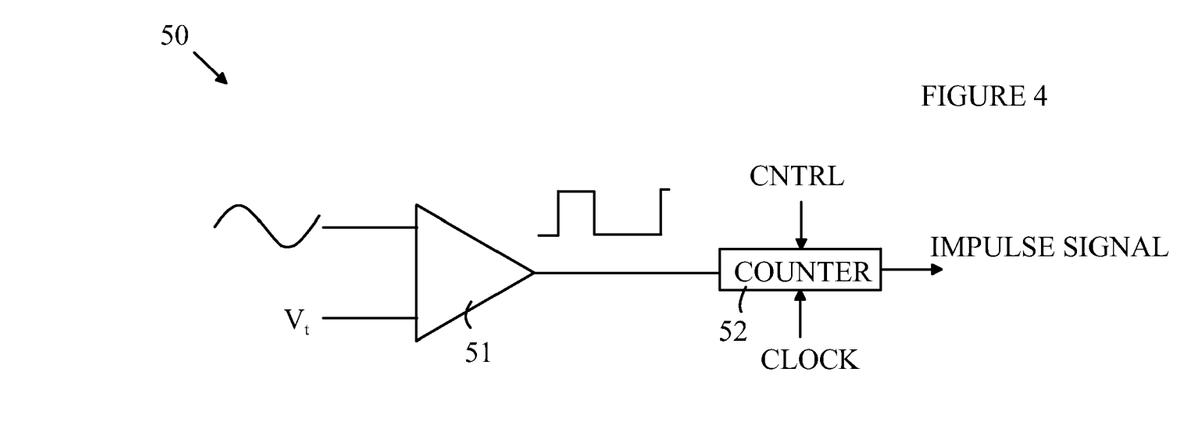
FIG. 4 illustrates a digital signal generator that generates a count that is proportional to the time that the cantilever arm signal is above a predetermined threshold.

A digital impulse signal can be generated by counting the clock pulses that occur during the time at which the cantilever arm signal is above the threshold level. Refer now to FIG. 4, which illustrates a digital signal generator that generates a count that is proportional to the time that the cantilever arm signal is above a threshold $V_t$. Signal generator 50 uses a comparator 51 to generate a control signal that causes counter 52 to count clock cycles. The contents of counter 52 are reset prior to the cantilever arm signal going positive. The contents of the counter are readout to provide a digital impulse signal.

Figure 5:
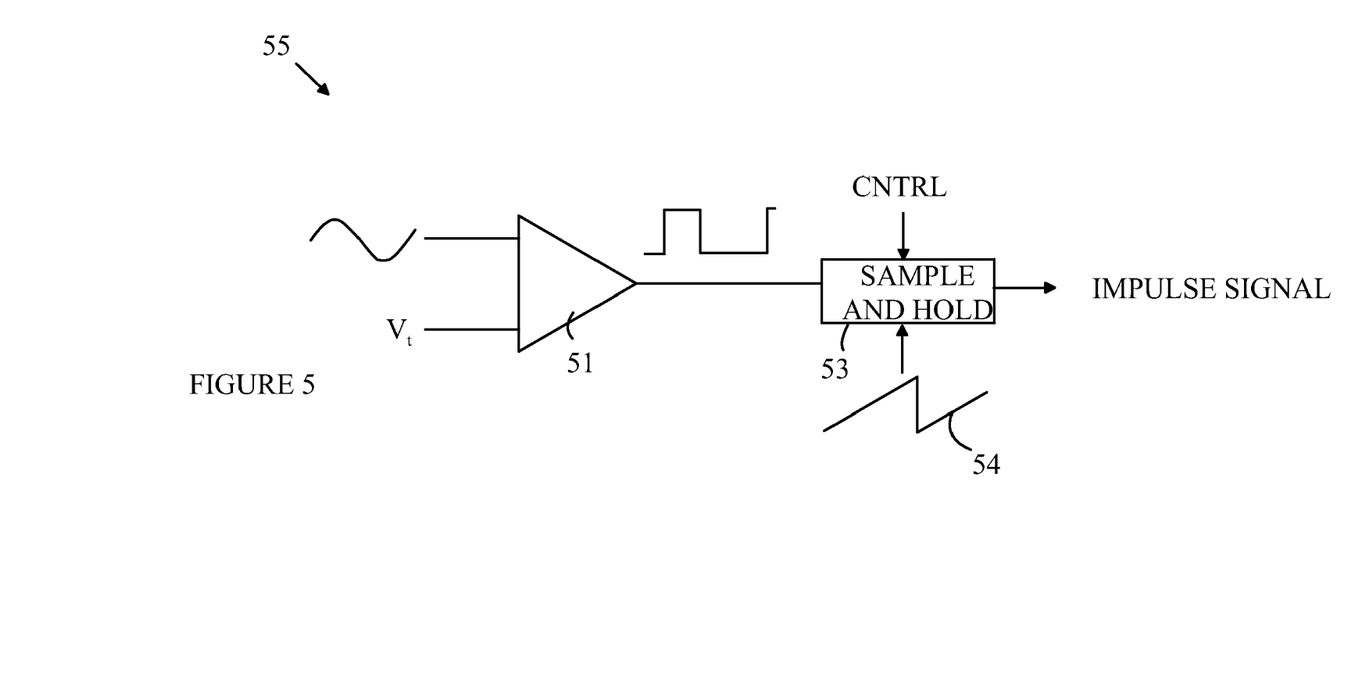
FIG. 5 illustrates an analog signal generator that can be used to generate the impulse signal.

An analog impulse signal can be generated by a similar circuit by replacing counter 52 with a sample and hold circuit. Refer now to FIG. 5, which illustrates an analog signal generator that can be used to generate the impulse signal. Signal generator 55 utilizes a sample and hold circuit 53 that samples a linearly increasing waveform 54 while an input signal generated by comparator 51 is positive. Sample and hold circuit 53 is reset by processor 41 during the time period in which the output of comparator 51 is low.

Similarly, processor 41 can measure the times at which the drive signal crosses zero, or some other reference potential, and compare those times to the times the cantilever arm signal crosses zero, or some other reference potential. The zero crossing points are preferred because these are more easily defined.

Figure 6:
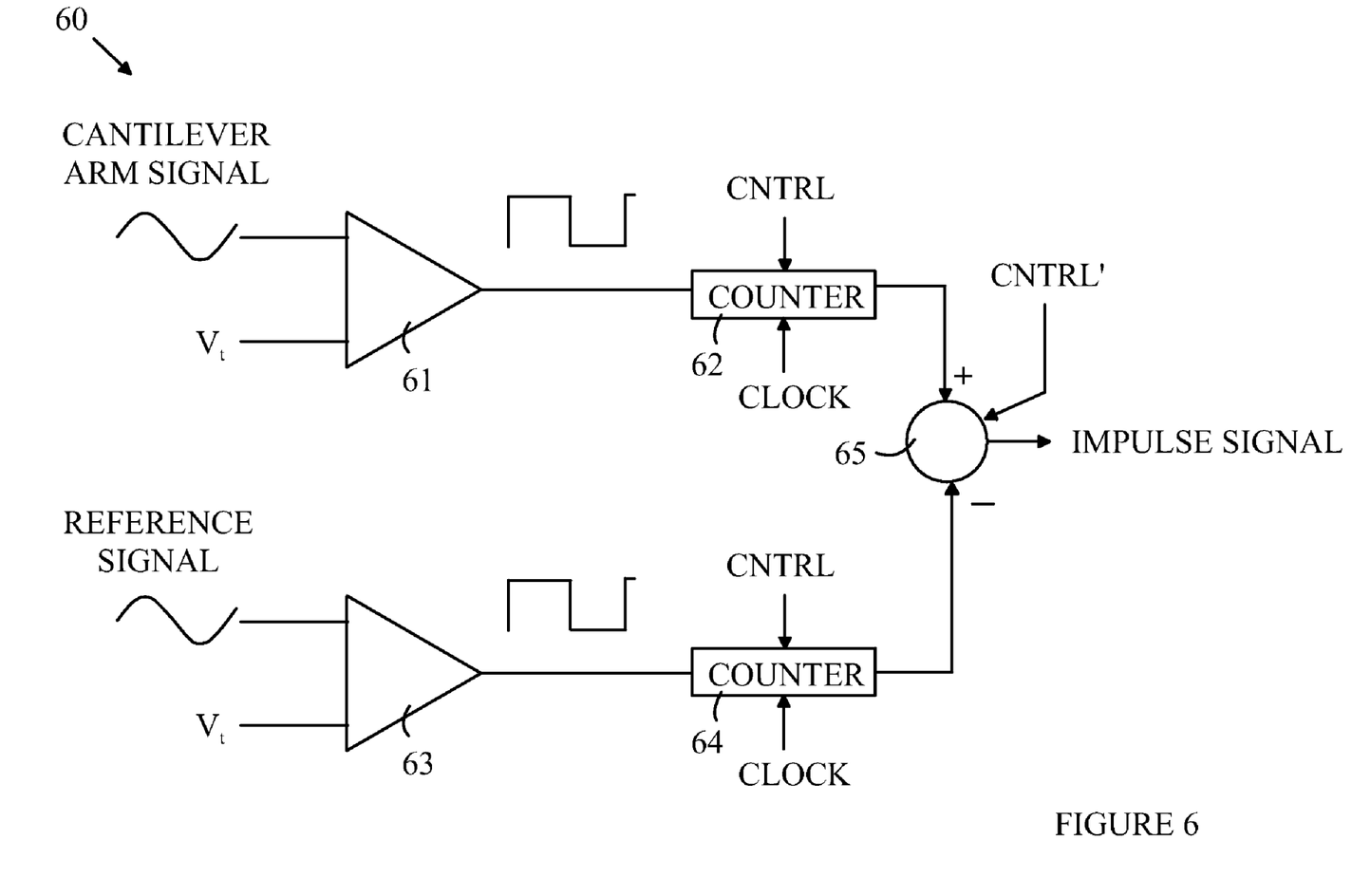
FIG. 6 illustrates another embodiment of a digital signal generator for generating an impulse signal that can be utilized in the present invention.

Two digital signal generators of the type shown in FIG. 4 can be combined to provide a circuit that outputs a count that is the difference between the times the cantilever arm signal crosses a predetermined threshold and the time at which the reference signal crosses that threshold. Refer now to FIG. 6, which illustrates another embodiment of a digital signal generator for generating an impulse signal that can be utilized in the present invention. Signal generator 60 uses a comparator 61 to generate a control signal that causes counter 62 to count clock cycles when the cantilever arm signal is above $V_t$. Signal generator 60 uses a second comparator 63 to generate a control signal that causes counter 64 to count clock cycles when the reference signal is above $V_t$. The contents of counter 64 is subtracted from the contents of counter 62 by circuit 65 in response to an appropriate control signal, CNTRL', to generate the impulse signal.

In another aspect of the invention, processor 41 measures the cantilever arm signal when the cantilever is sufficiently above the specimen to assure that the interaction force is negligible. This reference signal is examined to determine the times at which the cantilever arm signal crosses zero. These reference times are then compared with the zero crossing times observed when the cantilever is moved to a position at which the tip is subjecting the sample to a measurable interaction force to provide the impulse signal.

The above-described embodiments utilize the time points at which the cantilever arm signal crosses some predefined level to measure the distortion in the cantilever arm signal arising from the interaction of the probe tip and the specimen. To reduce errors resulting from noise in the cantilever arm signal, the cantilever arm signal can be fitted to a locally smooth function in the vicinity of the zero-crossing points.

Figure 7:
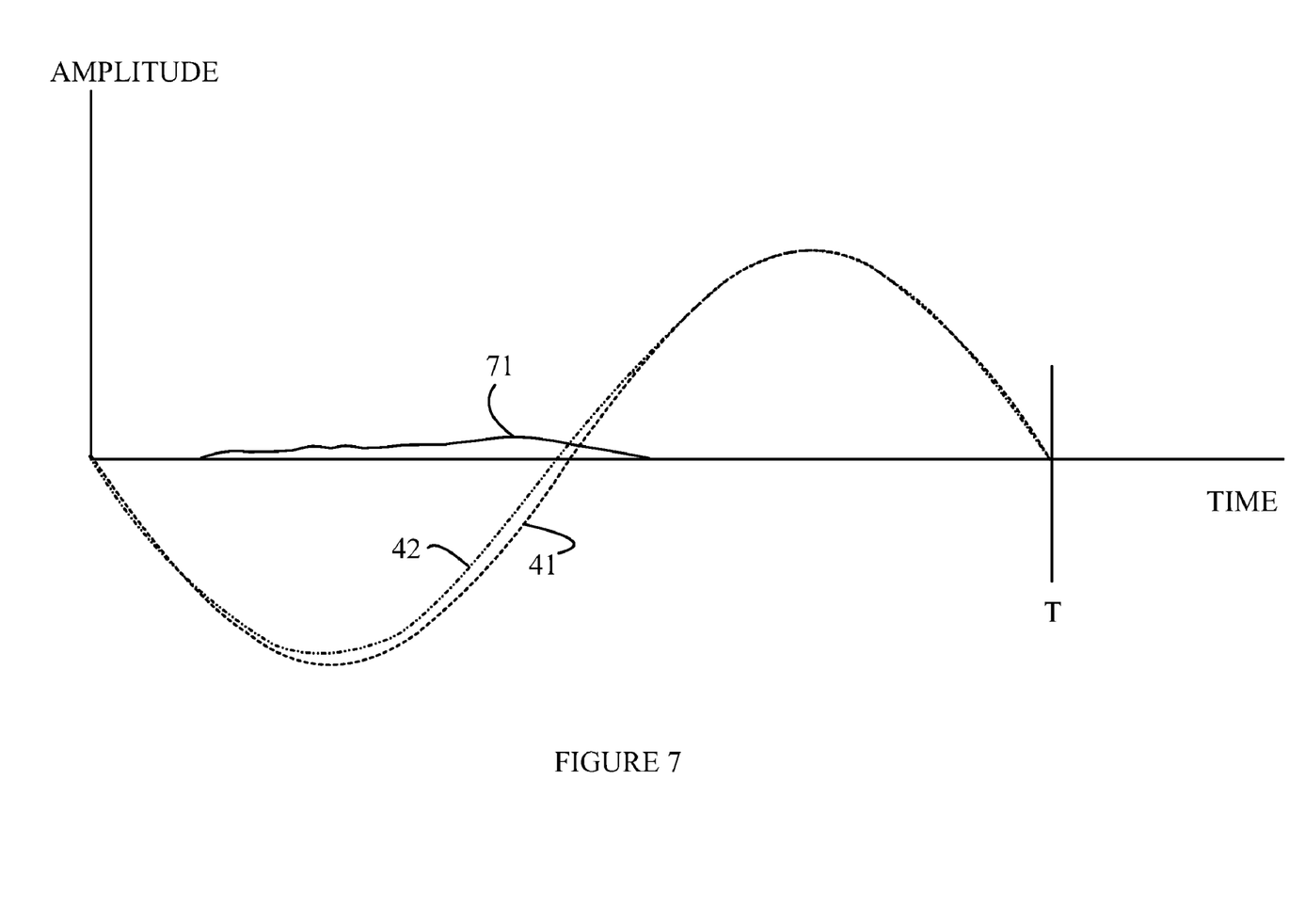
FIG. 7 illustrates the distortion for the case shown in FIG. 2.

However, other measurements of the distortion could be utilized. Refer now to FIG. 7, which illustrates the distortion for the case discussed above with respect to FIG. 2. For example, the difference between the cantilever arm signal when the tip is near the specimen and a reference calibration cantilever arm signal measured when the tip far from the specimen could integrated for a time period encompassing a significant fraction of one cycle to provide the impulse signal. The difference of these two signals can be viewed as a distortion function that measures the impulse over a significant fraction of one period of the cantilever arm signal. This distortion function is shown at 71 in FIG. 7. The amplitude of the reference signal can be scaled based on the average amplitude of the cantilever arm signal when the tip is interacting with the sample.

The distortion function also depends on the time alignment of the cantilever arm signal and the reference signal in time. The signals can be aligned by matching the signals over the portion of the cycle in which the tip is farthest from the sample. The distortion signal can be integrated in time to provide an impulse signal is less subject to noise.

Distortion measurements based on additional properties of the cantilever arm signal could also be utilized. For example, a function that depends of the position of the probe tip and the tip velocity could also be utilized to detect changes in the force of interaction between the tip and the specimen. In this case, this new function would be compared with a reference function obtained by measuring the same function when the tip is far from the specimen.

In the above-described embodiments, the sample is moved by the electro-mechanical actuator in all three directions. However, embodiments in which the actuator includes a first actuator that moves the cantilever arm in the z-direction while a second actuator moves the sample in the x-y plane could also be constructed. In addition, the actuator could move the cantilever in all three directions.

In the above-described embodiments, the cantilever arm assembly is shown as being attached to the shaker element 24 shown in FIG. 1. The attachment can be made through a probe mount that allows different probe and cantilever arm configurations to be removably attached to the shaker element.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. A scanning probe microscope comprising:
   a probe mount adapted to receive a probe having a tip that moves in response to an interaction between said tip and a local characteristic of a sample, said probe tip being mounted on a first end of a cantilever arm, a second end of said cantilever arm being coupled to said probe mount;

a mechanical vibrator that causes said second end of said cantilever arm to vibrate a predetermined frequency in response to a drive signal;

an electro-mechanical actuator that changes the distance between the sample and said second end of said cantilever arm;

a probe position signal generator that generates a position signal indicative of a position of said probe tip relative to said second end of said cantilever arm; and an impulse signal generator that measures a quantity related to an impulse imparted to said probe tip by said interaction between said tip and said local characteristics of said sample.

2. The microscope of claim 1 further comprising a servo that operates said electro-mechanical actuator so as to maintain said measured quantity at a predetermined value.

3. The microscope of claim 1 wherein said impulse signal generator measures a change in said position signal that occurs within 2 cycles of said drive signal after said interaction between said tip and sample changes.

4. The microscope of claim 1 wherein said impulse signal generator measures a time difference between successive times at which said position signal is equal to a first predetermined threshold value.

5. The microscope of claim 4 wherein said impulse signal generator compares said time difference with a time difference measured when said probe tip is positioned far from said sample.

6. The microscope of claim 4 wherein said impulse signal generator compares said time difference with a drive signal time difference corresponding to a time difference between successive times at which said drive signal is equal to a second predetermined threshold value.

7. The microscope of claim 1 wherein said impulse signal generator stores a measurement of said tip position signal as a function of time when said probe tip is far from said sample and wherein said impulse signal generator generates said impulse signal by measuring a difference between said tip position signal and said stored measurement.

8. The microscope of claim 1 wherein said impulse signal generator compares said tip position signal with said drive signal.

9. The microscope of claim 1 wherein said impulse signal generator stores a measurement of said position signal as a function of time when said probe tip is contacting the sample at a predetermined level of interaction and wherein said impulse signal generator generates said impulse signal by measuring a difference between said position signal and said stored measurement.

10. The microscope of claim 1 wherein said impulse signal generator stores a quantity derived from said position signal as a function of time when said tip is far from said sample and wherein said impulse signal generator generates said impulse signal by measuring a difference between said quantity and a value calculated from said tip position signal.

11. The microscope of claim 1 wherein said impulse signal generator measures said position signal when said probe tip is in a first state of interaction with said sample to generate a first signal, measures said position signal when said probe tip is in a second state of interaction with said sample to generate a second signal, and aligns said first signal with said second signal prior to measuring said quantity related to said impulse.

12. The microscope of claim 10 wherein said quantity is related to a time difference between zero crossings of said position signal as a function of time and a sine wave of a predetermined frequency.

13. The microscope of claim 11 wherein said probe tip is in intermittent contact with said sample in said first state.

* * * * *